United States Patent [19]

Jasys

[11] 4,444,686
[45] Apr. 24, 1984

[54] CRYSTALLINE PENICILLIN ESTER INTERMEDIATE

[75] Inventor: Vytautas J. Jasys, New London, Conn.

[73] Assignee: Pfizer Inc., New York, N.Y.

[21] Appl. No.: 434,290

[22] Filed: Oct. 14, 1982

Related U.S. Application Data

[63] Continuation-in-part of Ser. No. 341,081, Jan. 25, 1982, Pat. No. 4,381,263.

[51] Int. Cl.³ .......................................... C07D 499/32
[52] U.S. Cl. ................................. 260/239.1; 424/271
[58] Field of Search ...................................... 260/239.1

[56] References Cited

U.S. PATENT DOCUMENTS

| 4,234,579 | 11/1980 | Barth | 424/246 |
| 4,244,951 | 1/1981 | Bigham | 424/250 |
| 4,342,772 | 8/1982 | Godtfredsen et al. | 424/271 |

FOREIGN PATENT DOCUMENTS

| 881675 | 8/1980 | Belgium . |
| 2044255 | 10/1980 | United Kingdom . |

*Primary Examiner*—Glennon H. Hollrah
*Assistant Examiner*—Vera C. Clarke
*Attorney, Agent, or Firm*—Charles J. Knuth; James M. McManus; Mark Dryer

[57] ABSTRACT

Crystalline chloromethyl 6-(alpha-1-methoxycarbonylpropen-2-ylaminophenylacetamido)penicillanate as an intermediate to antibacterial agents.

1 Claim, No Drawings

CRYSTALLINE PENICILLIN ESTER INTERMEDIATE

CROSS REFERENCE TO RELATED APPLICATION

This application is a continuation-in-part of application Ser. No. 341,081, filed Jan. 25, 1982, now U.S. Pat. No. 4,381,263.

FIELD OF THE INVENTION

This invention relates to a crystalline compound. More particularly, it relates to crystalline chloromethyl 6-(alpha-1-methoxycarbonylpropen-2-ylaminophenylacetamido)penicillanate, a useful intermediate in the synthesis of antibacterial agents.

DESCRIPTION OF THE ART

Despite the wide use and acceptance of penicillins and cephalosporins, beta-lactam antibiotics, in combating bacterial infections, there are certain members within the group that are not active against resistant microorganisms because of the organism's ability to produce a beta-lactamase enzyme which reacts with beta-lactam antibiotic to produce products devoid of antibacterial activity. However, certain substances have the ability to inhibit beta-lactamases, and when used in combination with a penicillin or cephalosporin can increase or enhance the antibacterial effectiveness of the antibiotic against certain beta-lactamase producing microorganisms.

West German Offenegungsschrift No. 2,824,535 published Dec. 14, 1978 teaches that pencillanic acid sulfone is such an effective beta-lactamase inhibitor. In addition, it is taught in said application that certain esters of penicillanic acid sulfone are readily hydrolyzable in vivo giving high blood levels of this beta-lactamase inhibitor. Further, U.K. patent application No. 2,044,255 and U.S. Pat. No. 4,244,951 also teaches that halomethyl esters of penicillanic acid sulfone can be coupled through the carboxy group of an antibacterial penicillin to give compounds with readily hydrolyzable esters which degrade in vivo into antibacterial penicillins and the beta-lactamase inhibitor penicillanic acid sulfone.

In preparing penicillin intermediates it is frequently found that these compounds are viscous oils or amorphous solids. Such forms are, in general, more susceptible to decomposition and discoloration than is the crystalline form of the same compound. This propensity for decomposition by amorphous compounds, especially when they are employed as intermediates precludes stock-piling quantities of these compounds. In addition, when an amorphous intermediate compound is prepared it is frequently necessary to avoid storage of the compound and to employ it as soon as possible in the next reaction step. Further, the decomposition of amorphous intermediates ultimately leads to final products containing unwanted impurities.

SUMMARY OF THE INVENTION

It has now been found that a key intermediate in preparing 6'-(alpha-aminophenylacetamido)penicillanoyloxymethyl penicillanate 1,1-dioxide, namely, chloromethyl 6-(alpha-1-methoxycarbonylpropen-2-ylaminophenylacetamido)penicillanate of the formula

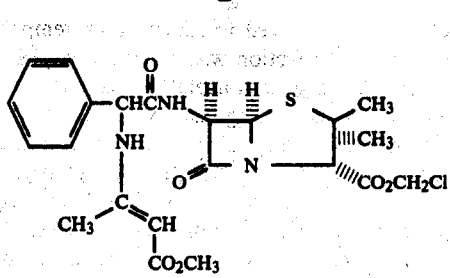

can be obtained in crystalline form.

DETAILED DESCRIPTION OF THE INVENTION

Chloromethyl 6-(alpha-1-methoxycarbonylpropen-2-ylaminophenylacetamido)penicillanate is prepared by reacting the tetrabutylammonium salt of 6-alpha-1-methoxycarbonylpropen-2-ylaminophenylacetamido)-penicillanic acid with excess of chloroiodomethane. The product is isolated as a yellow oil by column chromatography on silica gel using ethyl acetate/hexane as the eluent.

On rechromatographing, using the same type of stationary and mobile phases, the isolated product can be induced to crystallize from a mixture of diethyl ether/petroleum ether, using conventional techniques. Once crystalline, the aforementioned intermediate can also be recrystallized from diethyl ether alone.

In a similar manner chloromethyl 6-(alpha-1-methoxycarbonylpropen-2-ylamino-p-hydroxy-phenylacetamido)penicillanate, also a useful intermediate in preparing antibacterial agents possessing beta-lactamase inhibiting characteristics, can be prepared in crystalline form, thereby imparting greater stability to the compound.

As previously mentioned, U.S. Pat. No. 4,244,951 teaches that the halomethyl penicillanate sulfones, products of the presently claimed process, can be coupled with a variety of beta-lactam antibiotics to provide in vivo antibacterial agents which result from the absorption and subsequent hydrolysis of the coupled product to give high blood and tissue levels of penicillanic acid sulfone and the beta-lactam antibiotic resulting from said hydrolysis. In addition, the aforementioned U.K. application teaches how to use the products resulting from a coupling of penicillanic acid sulfone and a beta-lactam antibiotic.

The following examples are provided solely for the purpose of further illustration. Nuclear magnetic resonance spectra (NMR) were measured at 60 MHz for solutions in deuterochloroform (CDCl$_3$), perdeutero dimethyl sulfoxide (DMSO-d$_6$) or deuterium oxide (D$_2$O) or are noted otherwise, and peak positions are expressed in parts per million (ppm) downfield from tetramethylsilane or sodium 2,2-dimethyl-2-silapentane-5-sulfonate. The following abbreviations for peak shapes are used: b, broad; s, singlet; d, doublet; t, triplet; q, quartet; m, multiplet.

EXAMPLE 1

Crystalline chloromethyl 6-(alpha-1-methoxycarbonylpropen-2-ylaminophenylacetamido)penicillanate To 175 ml of chloroiodomethane was added 42.9 g of tetrabutylammonium 6-(alpha-1-methoxycarbonylpropen-2-ylaminophenylacetamido)penicillanate and the resulting mixture allowed to stir at room temperature for one hour. The reaction was chromatographed on 1 kg of silica gel using ethyl acetate/hexane (4:1, v:v) as the eluent, 250 ml cuts being made. Fractions 5-13 were combined and concentrated in vacuo to a yellow oil. The residue was rechromatographed using ethyl acetate/hexane (1:1, v:v). The fractions containing the product were combined and concentrated under vacuum to dryness. The residue was crystallized from diethyl ether/petroleum ether to give 16.4 g of crystalline product, m.p. 77°-79° C.

The NMR spectrum (CDCl$_3$) showed absorption at 1.5 (s, 3H), 1.57 (s, 3H), 1.9 (s, 3H), 3.65 (s, 3H), 4.4 (s, 1H), 4.65 (s, 1H), 5.12 (d, 1H), 5.42-5.7 (m, 2H), 5.75 (dd, 2H), 6.8 (d, 1H), 7.4 (s, 5H) and 9.35 (d, 1H) ppm.

EXAMPLE 2

6'-(alpha-Aminophenylacetamido)-penicillanoyloxymethyl penicillanate 1,1-dioxide p-toluenesulfonate A mixture of 496 mg of chloromethyl 6-(alpha-1-methoxycarbonylpropen-2-ylaminophenylacetamido)-penicillanate and 750 mg of sodium iodide in 10 ml of acetone was allowed to stir at room temperature overnight. The solvent was removed *in vacuo* and the residue extracted with 40 ml of ethyl acetate. The extract was washed successively with water (3×10 ml) and an aqueous saturated sodium chloride solution (2×5 ml), and then dried over sodium sulfate. The oil remaining (700 mg) after the solvent was removed was triturated with petroleum ether to give iodomethyl 6-(alpha-1-methoxycarbonylpropen-2-ylaminophenylacetamido)-penicillanate as a solid.

A mixture of 590 mg of iodomethyl 6-(alpha-1-methoxycarbonylpropen-2-ylaminoacetamido)penicillanate and 474 mg of tetrabutylammonium penicillanate sulfone was allowed to stir in 10 ml of acetone for 20 minutes. The reaction mixture was concentrated to dryness and the residue treated with 40 ml of ethyl acetate. The resulting precipitate was filtered, and the filtrate washed with water (3×10 ml) and a brine solution (2×5 ml). The dried organic phase was concentrated to about 20 ml and was treated with 190 mg of p-toluenesulfonic acid monohydrate and 2 drops of water in 5 ml of ethyl acetate. Stirring was continued for 3-4 minutes at which time a precipitate formed. After stirring for 10 minutes the desired product is filtered and dried, 520 mg.

The NMR spectrum (DMSO-D$_6$) showed absorption at 1.38 (s, 6H), 1.5 (s, 6H), 2.3 (s, 3H), 3.05-3.9 (m, 2H), 4.4 (s, 1H), 4.5 (s, 1H), 4.95-5.3 (m, 2H), 5.35-5.7 (m, 2H), 5.9 (s, 2H), 7.08 (d, 2H), 7.55 (d, 2H), 7.44 (d, 2H), 8.6-9.0 (ds, 3H) and 9.4 (d, 1H) ppm.

PREPARATION 1

Tetrabutylammonium 6-(alpha-1-methoxycarbonylpropen-2-ylaminophenylacetamido)penicillanate To 125 ml of methylene chloride and 50 ml of water was added 8.06 g of 6-(alpha-aminophenylacetamido)-penicillanic acid trihydrate and the pH adjusted to 8.5 by the addition of a 40% tetrabutylammonium hydroxide solution in water. The methylene chloride layer was separated and the aqueous layer was extracted with fresh methylene chloride (2×30 ml). The methylene chloride layers were combined and dried over magnesium sulfate.

The mixture was filtered and the filtrate concentrated *in vacuo*. Chloroform (300 ml), methyl acetoacetate (2.16 ml) and magnesium sulfate (20 g was added to the residue and the mixture heated to reflux for 30 minutes. The magnesium sulfate was filtered and the filtrate concentrated under reduced pressure to give a yellow foam. Treatment of the residue with 150 ml of ethyl acetate gave a white solid which was filtered, washed with ethyl acetate (3×25 ml) and diethyl ether (2×50 ml) and dried under nitrogen to give 6.5 g of the tetrabutylammonium 6-(alpha-1-methoxycarbonylpropen-2-ylaminophenylacetamido)penicillanate.

I claim:
1. A crystalline compound of the formula

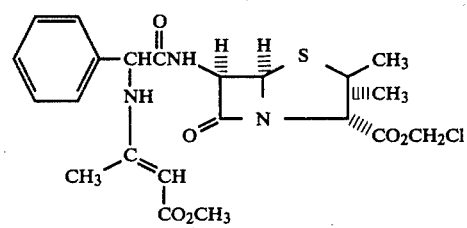

* * * * *